United States Patent [19]

Ueno et al.

[11] Patent Number: 5,523,461
[45] Date of Patent: Jun. 4, 1996

[54] STABILIZATION OF A PROSTANOIC ACID COMPOUND

[75] Inventors: Ryuji Ueno; Ryu Hirata, both of Hyogo-Ken, Japan

[73] Assignee: R-Tech Ueno, Ltd., Osaka, Japan

[21] Appl. No.: 202,132

[22] Filed: Feb. 25, 1994

[51] Int. Cl.$^6$ .................................................. A61K 31/557
[52] U.S. Cl. ............................................ 560/121; 502/503
[58] Field of Search ............................ 560/121; 562/503

[56] References Cited

U.S. PATENT DOCUMENTS

| | | |
|---|---|---|
| 3,829,579 | 8/1974 | Stehle et al. . |
| 4,358,603 | 11/1982 | Yu . |
| 5,166,175 | 11/1992 | Ueno .................................. 514/530 |
| 5,185,374 | 2/1993 | Ueno .................................. 514/530 |
| 5,317,032 | 5/1994 | Ueno .................................. 514/530 |

FOREIGN PATENT DOCUMENTS 0455264  11/1991  European Pat. Off. .

OTHER PUBLICATIONS

*Journal of Biological Chemistry*, vol. 250, No. 8, 1975, pp. 2789–2794.
*Lancet*, vol. 8037, 1977, p. 558.
*Lipids*, vol. 8, No. 10, pp. 592–594 (1973).

*Primary Examiner*—Robert Gerstl
*Attorney, Agent, or Firm*—Sughrue, Mion, Zinn, Macpeak & Seas

[57] ABSTRACT

The present invention provides a method of stabilizing a prostanoic acid compound, wherein the prostanoic acid compound having at least one oxo group on the ω chain are stored in a hydrous condition.

2 Claims, No Drawings

STABILIZATION OF A PROSTANOIC ACID COMPOUND

BACKGROUND OF THE INVENTION

The present invention relates to enhancement of stability of a prostanoic compound acids having at least one oxo group on the ω chain.

Generally, quality of a pharmaceutical product is controlled based on the policy that contamination should be prevented and that the quality of the product should be consistent. Accordingly, the product should have at least a certain degree of purity which can be maintained for a certain period. This is important especially in the case of a compound exhibiting a physiological activity in a small amount, such as a prostanoic acid compound.

The Prostanoic acid compound, which have general structural characteristics of naturally-occurring prostaglandins (PGs), are represented by the following formula.

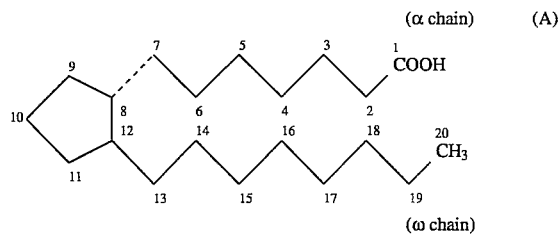

According to structure of the 5-membered ring, natural PGs can be classified into PGAs, PGBs, PGCs, PGDs, PGEs, PGFs, PGGs, PGHs, PGIs and PGJs. They are further grouped, based on the unsaturations at 5, 6 positions and at 13, 14 positions, into $PG_1s$ (13,14-unsaturated), $PG_2s$ (5,6 and 13,14-diunsaturated) and $PG_3s$ (5,6-, 13,14- and 17,18- triunsaturated).

PGFs are further classified according to the configuration of hydroxyl group at 9 position into α form (hydroxyl group present in alfa configuration) and β form (hydroxyl group present in beta configuration).

Although these natural PGs have various pharmacological activities, they are commonly unstable, and are liable to be decomposed by acids, bases or heat. Moisture is also a factor affecting the stability of PGs, and PGs should be stored in an anhydrous condition or in a condition in which the moisture content is as low as possible.

SUMMARY OF THE INVENTION

It was found that stability of a prostanoic acid compound having at least one oxo group on the ω chain can be enhanced by storing it in a hydrous condition unlike to natural PGs.

Accordingly, the present invention provides a method of stabiling a prostanoic acid compound comprising storing the prostanoic acid compound having at least one oxo group on the ω chain in a hydrous condition.

DETAILED DESCRIPTION OF THE INVENTION

The present invention relates to method of stabilizing a prostanoic acid compound, in which the prostanoic acid compound which have at least one oxo group on the ω chain are kept in a hydrous condition.

In the present invention, the prostanoic acid compound having at least one oxo group on the ω chain mean compounds in which at least one oxo group are present as a substituent in the ω chain moiety of the prostanoic acid compound represented by formula (A) shown above. These compounds may contain any modification described hereinafter or others.

Nomenclature of the prostanoic acid compound herein uses the numbering system of prostanoic acid represented in formula (A) shown above.

While formula (A) shows a basic skeleton having twenty carbon atoms, the compound used in the present invention are not limited to those having the same number of carbon atoms. The carbon atoms in Formula (A) are numbered 2 to 7 on the α-chain starting from the α-carbon atom adjacent to the carboxylic carbon atom which is numbered 1 and towards the five-membered ring, 8 to 12 on the said ring starting from the carbon atom on which the α-chain is attached, and 13 to 20 on the ω-chain starting from the carbon atom adjacent to the ring. When the number of carbon atoms is decreased in the α-chain, the number is deleted in order starting from position 2 and when the number of carbon atoms is increased in the α-chain, compounds are named as substituted derivatives having respective substituents at position 1 in place of carboxy group (C-1). Similarly, when the number of carbon atoms is decreased in the ω-chain, the number is deleted in order starting from position 20 and when the number of carbon atoms is increased in the ω-chain, compounds are named as substituted derivatives having respective substituents at position 20. Stereochemistry of the compounds is the same as that of above formula (A) unless otherwise specified.

In general, PGD, PGE and PGF are the compounds having hydroxyl groups at 9 and/or 11 positions, but in the present specification the term "prostanoic acid compound" also includes those having other groups at 9 and/or 11 positions instead of hydroxyl groups. Such compounds are designated nomenclaturally as 9-dehydroxy-9-substituted derivatives or 11-dehydroxy-11-substituted derivatives.

The prostanoic acid compound according to the present invention are designated nomenclaturally based on the skeleton of the prostanoic acids as described above. When the compounds have the moiety identical structurally to prostaglandin, abbreviation of PG may be employed conveniently. For example, 13,14-dihydro-15-keto-16R, S-fluoro-$PGE_2$ is designated according to IUPAC nomenclature as (Z)-7-{(1R, 2R, 3R)-3-hydroxy-2-[(4R, S)-4-fluoro-3-oxooctyl]-5-oxocyclopentyl}hept-5-enoic acid; 13,14-dihydro-15-keto-20 -ethyl-11-dehydroxy-11R-methyl-$PGE_2$ methyl ester as methyl (Z)-7-{(1R,2R,3R)-3-methyl-2-[3-oxodecyl]-5-oxocyclopentyl}hept-5-enoate; 13,14-dihydro-6,15-diketo-19-methyl-$PGE_1$ ethyl ester as ethyl 7{(1R,2R, 3R)-3-hydroxy-2 -(7-methyl-3-oxooctyl)-5-oxocyclopentyl)-6-oxoheptanoate; 13,14-dihydro-15-keto-20-ethyl-$PGF_2α$ isopropyl ester as isopropyl (Z)-7-[(1R,2R, 3R,5S)-3,5-dihydroxy-2 {3-oxodecyl-}cyclopentyl]hept-5-enoate: and, 13,14-dihydro-15-keto-20 -methyl-$PGF_2α$ methyl ester as methyl (Z)-7[(1R,2R,3R, 5S)-3,5-dihydroxy-2-(3-oxononyl)-cyclopentyl]hept-5-enoate.

The prostanoic acid compound having at least one oxo group on ω chain in the present invention are preferably one in which the carbon atom at 15 or 16 position of the prostanoic acid compound forms a carbonyl group. The compounds having oxo groups at the positions other than, or, in addition to the position described above (for example, 17, 18, 19 positions and the like) may also be employed.

The compounds may be those in which the carboxylic acid at the end of the a chain of the prostanoic acids described above is esterified, pharmacologically acceptable salts, those in which double bond between 2 and 3 positions or triple bond between 5 and 6 positions is present, those having substituents on the carbon atoms at 3, 6, 16, 17, 19 and/or 20 positions, those having lower alkyl group or hydroxy (lower) alkyl group instead of hydroxyl group at 9 and/or 11 positions.

The substituents on the carbon atoms at 3 and/or 19 positions may be, for example, alkyl groups having 1 to 4 carbon atoms, particularly methyl and ethyl groups. The substituents on the carbon atoms at 16 and/or 17 positions may be, for example, lower alkyl groups such as methyl and ethyl, hydroxyl group, halogens such as chlorine and fluorine, aryl groups such as phenyl group, and aryloxy groups such as trifluoromethylphenoxy. The substituents on the carbon atom at position 20 are, for example, saturated or unsaturated lower alkyl groups such as $C_{1-4}$ alkyl, lower alkoxy groups such as $C_{1-4}$ alkoxy, and lower alkoxyalkyl groups such as $C_{1-4}$ alkoxy-$C_{1-4}$ alkyl. The substituents on the carbon atom at 6 position include oxo group forming a carbonyl group. Configuration of a compound having hydroxyl group, lower alkyl group or lower(hydroxy)alkyl substituents on the carbon atoms at 9 and/or 11 positions may be α form or β form or mixture thereof.

In addition, the compounds mentioned above may be those having substituents such as alkoxy, phenoxy and phenyl group at the end of the ω chain which is shorter than that of a natural PG.

Particularly preferred compounds employed in the present invention are those represented by the formula (I):

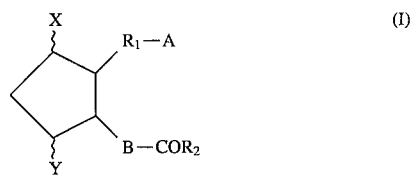

wherein

X and Y are hydrogen, hydroxy, halogen, lower alkyl, hydroxy(lower)alkyl or oxo (provided that at least one of X and Y is other than hydrogen, and the 5-membered ring may have at least one double bond);

A is COOH and salts or esters thereof;

B is —$CH_2$—$CH_2$—, —CH=CH—, —C≡C—, —$CH_2$—$CH_2$—$CH_2$—, —$CH_2$—CH=CH—, —$CH_2$—C≡C—, —CH=CH—$CH_2$— or —C≡C—$CH_2$—;

$R_1$ is a divalent saturated or unsaturated lower or medium aliphatic hydrocarbon residue which is unsubstituted or substituted with a halo, oxo or aryl group.

$R_2$ is a saturated or unsaturated, lower or medium aliphatic hydrocarbon residue which is unsubstituted or substituted with halo, hydroxy, oxo, lower alkoxy, lower alkanoyloxy, cyclo (lower)alkyl, aryl or aryloxy group.

In the above formula, the term "unsaturated" in the definitions for $R_1$ and $R_2$ is intended to include at least one and optionally more than one double bond and/or triple bond isolatedly, separately or serially present between carbon atoms of main and/or side chain. According to usual nomenclature, and unsaturation between two serial positions is represented by denoting younger number of said two positions, and an unsaturation between two distal positions is represented by denoting both of the positions. Preferred unsaturation is a double bond at position 2 and a double or triple bond at position 5.

The term "lower or medium aliphatic hydrocarbons" refers to a straight or branched chain hydrocarbonyl group having 1 to 14 carbon atoms (for a side chain, 1 to 3 carbon atoms being preferred) and preferably 2 to 8 carbon atoms for $R_1$ and 1 to 9 carbon atoms for $R_2$.

The term "halogen" includes fluorine, chlorine, bromine and iodine.

The term "lower" includes a group having 1 to 6 carbon atoms unless otherwise specified.

The term "lower alkyl" includes straight or branched, saturated hydrocarbon groups having 1 to 6 carbon atoms, such as, methyl, ethyl, propyl, isopropyl, butyl, isobutyl, t-butyl, pentyl and hexyl.

The term "lower alkoxy" is used for lower alkyl-O-phenyls in which the moiety of lower alkyl is defined as described above.

The term "hydroxy(lower)alkyl" means an alkyl group defined as above substituted with at least one hydroxy group, such as hydroxymethyl, 1-hydroxyethyl, 2-hydroxyethyl and 1-methyl-1-hydroxyethyl.

The term "lower alkanoyloxy" means a group represented by the formula: RCO—O— [wherein RCO— is acyl generated from a lower alkyl defined above by oxidation, such as acetyl].

The term "cyclo-lower alkyl" means a cyctic group formed by cyclization of a lower alkyl groups as deffined above.

The term "aryl" includes unsubstituted or substituted aromatic carbocyclic or heterocyclic groups (preferably monocyclic), such as phenyl, tolyl, xylyl and thienyl. The substituents include halogen atoms or halogen-substituted alkyl groups (where halogen atoms and lower alkyl groups are defined above).

The term "aryloxy" means a group represented by the formula: ArO— (wherein Ar is an aryl group as defined above).

The salts of the carboxylic group designated as A may be pharmaceutically acceptable salts.

Suitable "pharmaceutically acceptable salts" include traditionally-employed non-toxic salts, including salts with inorganic bases, such as alkaline metal salts (sodium and potassium salts, etc.), alkaline earth metal salts (calcium and magnesium salts, etc.) and ammonium salts, as well as salts with organic bases, such as amine salts (for example, salts with methylamine, dimethylamine, cyclohexylamine, benzylamine, piperidine, ethylenediamine, ethanolamine, diethanolamine, triethanolamine, tris(hydroximethylamino) ethane, monomethyl-monoethanolamine, lysine, procaine, caffeine, etc.) and salts with basic amino acids (for example, salts with arginine and lysine, etc.) and tetraalkylammonium salts. These salts may be produced from corresponding acids and bases by means of usual neutralization or salt exchange.

Esters may be aliphatic esters including lower alkylesters such as methyl ester, ethyl ester, propyl ester, isopropyl ester, butyl ester, isobutyl ester, t-butyl ester, pentyl ester and 1-cyclopropylethyl ester, lower alkenyl esters such as vinyl ester and allyl ester, lower alkynyl esters such as ethynyl ester and propynyl ester, hydroxy(lower)alkyl esters such as hydroxyethyl ester, lower alkoxy (lower) alkyl esters such as methoxymethyl ester and 1-methoxyethyl ester, and optionally substituted aryl esters such as phenyl ester, tolyl ester, t-butylphenyl ester, salicyl ester, 3,4-dimethoxy-phenyl ester and benzamidophenyl ester, as well as aryl(lower)-alkyl esters such as benzyl ester, trityl ester and benzhydryl ester.

These esters may be produced from corresponding acids and alcohols by means of usual esterification or ester exchange.

Examples of preferable group A are —COOH, —COOCH$_3$, —COOCH$_2$CH$_2$, and —COOCH(CH$_3$)$_2$.

In the formula (I) shown above, arrangements of α and/or ω chains may be similar to or different from those of natural prostaglandins. However, in the present invention, mixtures of the compound of natural configuration and the compounds of non-natural configuration may also be included.

Examples of the typical compounds according to the present invention are 15-keto(oxo)-PGAs to -PGFs and 20-lower alkyl derivatives, Δ$^2$-derivatives, 3R,S-methyl-derivatives, 6-keto-derivatives, 5R,S-fluoro-derivatives, 5,5 -difluoro-derivatives, 16R,S-methyl-derivatives, 16,16 -dimethyl-derivatives, 16R,S-fluoro-derivatives, 16,16 -difluoro-derivatives, 17S-methyl-derivatives, 17R,S-fluoro-derivatives, 17,17-difluoro-derivatives, 17-phenyl-derivatives and 19-methyl-derivatives.

Also included are 15-dehydroxy-16-keto(oxo)-PGAs to -PGFs and 20-lower alkyl derivatives, 17R,S-methyl-derivatives, 17,17-dimethyl-derivatives, 17R,S-fluoro-derivatives and 17,17-difluoro-derivatives.

15-keto- or 16-keto-PGs, which are included in the prostanoic acids of the present invention sometimes form hemiacetal formation between a hydroxy group at 11 position and a keto group at 15 or 16 position, whereby providing the keto-hemiacetal equilibrium.

When such tautomeric isomers are present, the ratio of both isomers varies depending on the structure of other moieties of a molecule and the types of the substituents, and one isomer may be predominant in some cases. In the present invention, all of such tautomeric isomers are included. Although a compound may be designated in the present invention using a structure or a nomenclature corresponding to a keto form regardless of the presence of such isomers for the purpose of convenience, the compounds of hemiacetal forms are not intended to be excluded.

In the present invention, individual tautomeric isomers and mixtures thereof, optical isomers and mixtures thereof, racemate, and other isomers such as stereoisomers may also be employed for the same purpose.

Some of the prostanoic acid compound as components of the present invention may be produced by the methods disclosed in Japanese Patent Appln. KOKAI S64-52753, Japanese Patent Appln. KOKAI H1-104040, Japanese Patent Appln. KOKAI H1-151552, Japanese Patent Appln. KOKAI H2-108, Japanese Patent Appln. KOKAI H2-96528, Japanese Patent Appln. H3-55930 and Japanese Patent Appln. H3-125253. These compounds may be produced according to methods described above optionally or in combination with known methods for ring formation.

The term "hydrous condition" means a condition where the prostanoic acid compound having at least one oxo group on the ω chain contain moisture in at least a certain amount sufficient to allow clear distinction from a dry product. Thus, according to the present invention, the prostanoic acid compound should contain moisture in a higher than a given percentage. Generally, this hydrous condition means a case where the moisture content of the prostanoic acid compound is about 1.0% by weight or more. Although the moisture content varies depending on the prostanoic acid compound employed, it is at least about 1.0% by weight, preferably at least about 2.0% by weight. On the other hand, when the preferable range of moisture content is represented as molar ratio based on the prostanoic acid employed, then the content is at least about 0.25 mole, preferably at least about 0.5 mole. The upper limit of the moisture content is not critical, and dissolution or suspension of the prostanoic acid compound in an excess amount of water may also provide the advantage of the present invention.

The method of incorporating water into prostanoic acids are not limitable. For example, a predetermined amount of water may be added to the compound and shaken, or the compounds may be allowed to stand under a moist condition. Alternatively, the prostanoic acid compound is added to an excess amount of water to form a suspension, or it is dissolved in water optionally with an aid of a solubilizer.

Accordingly, the present invention further provides a method of storing the prostanoic acid compound comprising incorporating moisture into prostanoic acids having at least one of oxo group on the ω chain in the moisture content of at least 1.0% by weight, and then allowing them to stand under such a moisture condition that the moisture content of the prostanoic acid compound can be kept at the almost equilibrated state, the prostanoic acid compound stored by this method, and a method of storing the prostanoic acid compound comprises keeping the prostanoic acid compound having at least one of oxo group on the chain in a closed space in the presence of water having an open water surface. The closed space means the inside of ampules, vials, sealed vessels and desiccators. To be placed in the presence of water having open water surface includes both of to be in contact with water and to be separated from water. Thus, a part of or all of the prostanoic acid compound may be present in water while floating, sedimenting, suspending and the like, or may be present separately from water in a single closed space in an ampule, vial, sealed vessel or desiccator.

A 15-oxo(keto) form may be produced from a commercially available (−) Corley lactone by Collins oxidation to form an aldehyde, which is then reacted with dimethyl(2-oxoalkyl) phosphonate anion to form and α, β-unsaturated ketone, which is then reduced to obtain a ketone, whose carbonyl group is then reacted with a diol to form a ketal for the purpose of protection, followed by de-p-phenylbenzoyl reaction to yield an alcohol, whose hydroxyl group newly generated is then protected with dihydropyrane to give tetrahydropyranyl ether. By this procedure, a precursor for a PG whose ω chain is 15-oxo(keto) form. A 16-oxo(keto) form may be produced by subjecting a commercially available (−) Corley lactone to carbon-increasing reaction to obtain a (−) Corley lacton extended by additional one carbon atom, which is then subjected to the procedure similar to that for 15-keto form, to give a precursor for a PG whose ω chain is 16-keto form.

Using tetrahydropyranyl ether described above as a starting material, a 6-keto-PG$_1$s having the moiety of the formula:

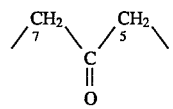

may be produced as follows:

Tetrahydropyranyl ether is reduced using, for example, diisobutylaluminum hydride to give a lactol, which is then reacted with a ylide obtained from (4-carboxybutyl)-triphenylphosphonium bromide, and the resultant is subjected to esterification followed by cyclization of the C$_5$–C$_6$ double bond with the hydroxyl group at 9 position using NBS or iodine to give a halide. The resultant is then dehalogenated using, for example, DBU to give 6-keto compound, which is then subjected to Jones oxidation followed by deprotection.

Furthermore, PG$_2$s having the moiety of the formula:

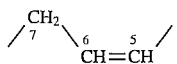

may be produced following steps:

Tetrahydropyranyl ether as described above is reduced to give a lactol, which is then reacted with a ylide obtained from (4-carboxybutyl)triphenylphosphonium bromide to give a carboxylic acid. The resultant is then esterified and subjected to Jone oxidation followed by deprotection.

Using tetrahydropyranyl ether described above as a starting material, PG$_1$s having the moiety of the formula:

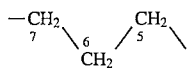

may be produced by conducting the reaction similarly as in the case of PG$_2$s having the moiety of the formula:

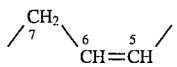

to give a compound, whose double bond at 5–6 position is then reduced catalytically prior to deprotection. Synthesis of a 5,6-dehydro-PG$_2$s having the carbon chain at 5,6 and 7 positions as follows:

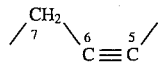

is achieved by capturing a copper enolate generated by 1,4-addition reaction of a monoalkyl copper complex or dialkyl copper complex of the formula:

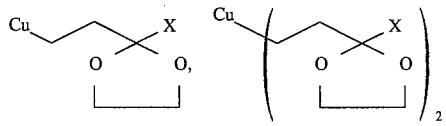

to 4R-t-butyldimethylsilyloxy-2-cyclopenten-1-on with 6-carboalkoxy-1-iodo-2-hexyne or its derivative.

In a method of preparing PGs having methyl group instead of hydroxyl group at 11 position, the hydroxyl group at 9 position of 11-tosylate form is subjected to Jones oxidation to yield PGA type compounds, to which dimethyl copper complex is then reacted to give a 11-dehydroxy-11-methyl-PGE type compound. Alternatively, an alcohol obtained after elimination of p-phenylbenzoyl group is converted into a rosylate. The obtained rosylate is then subjected to DBU treatment to give an unsaturated lactone, which is then converted into a lactol. After introduction of an α-chain using Wittig Reaction, the obtained alcohol (9 position) is oxidated to give PGAs, to which dimethyl copper complex is then reacted to give a 11-dehydroxy-11-methyl-PGEs. This may be reduced using, for example, sodium borohydride to obtain a 11-dehydroxy-11-methyl-PGFs.

PGs containing a hydroxymethyl group instead of a hydroxyl group at 11 position is obtained as follow:

11-dehydroxy-11-hydroxymethyl-PGE is obtained by a benzophenone-sensitized photoaddition of methanol to PGA. The resultant is, for example, reduced using sodium borohydride to give 11-dehydroxy-11-hydroxymethyl-PGF.

16-Fluoro-PGs may be obtained using dimethyl (3-fluoro-2-oxoalkyl)phosphonate anion in the preparation of an α, β-unsaturated ketone. Similarly, 19-methyl-PGs may be obtained using a dimethyl (6-methyl-2-oxoalkyl)-phosphonate anion.

PGs having phenyl at the end of the ω chain may be obtained by using a dimethyl(2-oxophenylalkyl)phosphonate anion.

Method of preparation according to the present invention is not limited to those described above, and any appropriate methods of protection, oxidation, reduction and the like may be employed.

PREPARATION EXAMPLE

Synthesis of 13,14-dihydro-15-keto-20-ethyl-PGA$_2$ isopropyl ester, 13,14-dihydro-15-keto-20-ethyl-PGE$_2$ isopropyl ester and 13,14-dihydro-15-keto-20-ethyl-PGF$_2$α isopropyl ester (Scheme I):

(1) Synthesis of 1S-2-oxa-3-oxo-6R-(3-oxo-1-transdecenyl)-7R-(4-phenylbenzoyloxy)-cis-bicyclo[3.3.0]octane (3):

A commercially available (−)- Corley lacton (1) (7 g) was subjected to Collins oxidation in dichloromethane to obtain an aldehyde (2), which is then reacted with dimethyl(2-oxononyl)phosphonate (4.97 g) anion to obtain 1S-2-oxa-3-oxo-6R-(3,3-ethylenedioxy-1-trans-decenyl)-7R-(4-phenylbenzoyloxy)-cis-bicyclo[3.3.0]octane (3).

(2) Synthesis of 1S-2-oxa-3-oxo-6R-(3-oxodecyl)-7R-(4-phenylbenzoyloxy)-cis-bicyclo[3.3.0]octane (4):

Unsaturated ketone (3) (7.80 g) was reduced in ethyl acetate (170 ml) using 5% Pd/C and hydrogen. After treatment by a standard method, a product (4) obtained was subjected to the next reaction.

(3) Synthesis of 1S-2-oxa-3-oxo-6R-(3,3-ethylene-dioxydecyl)-7R-(4-phenylbenzoyloxy)-cis-bicyclo[3.3.0]octane (5):

Saturated ketone (4) was converted in dry benzene (150 ml) using ethyleneglycol and p-toluenesulfonic acid (catalytic amount) into ketal (5).

(4) Synthesis of 1S-2-oxa-3-oxo-6R-(3,3-ethylene-dioxydecyl)-7R-hydroxy-cis-bicyclo[3.3.0]octane (6):

Ketal (5) was dissolved in absolute methanol (150 ml), to which then potassium carbonate (2.73 g) was added and stirred at room temperature overnight. After neutralization with acetic acid, the mixture was concentrated under reduced pressure. A crude product thus obtained was extracted with ethyl acetate, washed with dilute sodium bicarbonate and saline, and then dried. A crude product obtained by a standard treatment is chromatographed to obtain alcohol (6). Yield: 3.31 g (5) Synthesis of lactol (7):

Alcohol (6) (0.80 g) was reduced at −78° C. in dry toluene (8 ml) using DIBAL-H to obtain lactol (7).

(6) Synthesis of 13,14-dihydro-15,15-ethylenedioxy-20-ethyl-PGF$_2$α (8):

An ylide prepared from (4-carboxybutyl)triphenylphosphonium bromide (3.65 g) was admixed with a solution of lactol (7) in DMSO. After stirring the mixture overnight, carboxylic acid (8) was obtained.

(7) Synthesis of 13,14-dihydro-15,15-ethylenedioxy-20-ethyl-PGF$_2$α isopropyl ester (9):

Carboxylic acid (8) in acetonitrile was treated with DBU and isopropyl iodide to obtain 13,14-dihydro-15,15-ethylene-dioxy- 20-ethyl-PGF$_2$α isopropyl ester (9). Yield: 0.71 g (8) Synthesis of 13,14-dihydro-15-keto-20-ethyl-PGF$_2\alpha$ isopropyl ester (10):

13,14-dihydro-15,15-ethylenedioxy-20-ethyl-PGF$_2\alpha$ isopropylester (9) (0.71 g) was kept in acetic acid/THF/water (3/1/1) at 40° C. for 3 hours. The mixture was concentrated under reduced pressure to obtain a crude product, which was then chromatographed to obtain 13,14-dihydro-15-keto-20-ethyl-PGF$_2\alpha$ isopropyl ester (10). Yield: 0.554 g (9) Synthesis of 13,14-dihydro-15-keto-20-ethyl-PGA$_2$ isopropyl ester (12):

A solution of 13,14-dihydro-15-keto-20-ethyl-PGF$_2\alpha$ isopropyl ester (10) (0.125 g) and p-toluenesulfonyl chloride (0.112 g) in pyridine (5 ml) was kept at 0° C. for 2 days. Tosylate (11) was obtained by a standard treatment.

Tosylate (11) in acetone (8 ml) was subjected to Jones oxidation at −25° C. A crude product obtained after a standard treatment was chromatographed to obtain 13,14-dihydro-15-keto-20-ethyl-PGA$_2$ isopropyl ester (2). Yield: 0.060 g

(10) Synthesis of 13,14-dihydro-15,15-ethylenedioxy-20-ethyl-11-t-butyldimethylsiloxy-PGF$_2\alpha$ isopropyl ester (13):

13,14-dihydro-15,15-ethylenedioxy-20-ethyl-PGF$_2\alpha$ isopropyl ester (9) (3.051 g) was dissolved in N,N-dimethylformamide (25 ml) and t-butyldimethylsilyl chloride (1.088 g) and imidazole (0.49 g) were added, and then the mixture was stirred at room temperature overnight. The reaction mixture was concentrated under reduced pressure to obtain a crude product, which was then chromatographed to obtain 13,14-dihydro-15-ethylenedioxy-20-ethyl-11-t-butyldimethylsiloxy-PGF$_2\alpha$ isopropyl ester (13). Yield: 2.641 g

(11) Synthesis of 13,14-dihydro-15,15-ethylenedioxy-20-ethyl-11-t-butyldimethylsiloxy-PGE$_2$ isopropyl ester (14):

13,14-dihydro-15,15-ethylenedioxy-20-ethyl-11-t-butyldimethylsiloxy-PGF$_2\alpha$ isopropyl ester (13) (0.171 g) in methylene chloride was subjected to Collins oxidation (20 equivalents) at room temperature according to a usual workup. After 50 minutes, the reaction mixture was admixed with sodium hydrogen sulfate (1.15 g) and the mixture was filtrated. The filtrate was concentrated to obtain a crude product, which was then chromatographed (hexane/ethyl acetate 10:1). 13,14-dihydro-15,15-ethylenedioxy-20-ethyl-11-t-butyldimethylsiloxy-PGE$_2$ isopropyl ester (14) was obtained. Yield: 0.153 g (89%)

(12) Synthesis of 13,14-dihydro-15-keto-20-ethyl-PGE$_2$ isopropyl ester (15):

13,14-dihydro-15,15-ethylenedioxy-20-ethyl-11-t-butyldimethylsiloxy-PGE$_2$ isopropyl ester (14) (0.089 g) was dissolved in acetonitrile, and admixed with 46% aqueous solution (1 ml) of hydrofluoric acid at 0° C. The mixture was stirred at room temperature for 40 minutes. The reaction mixture was treated according to a standard procedure to obtain a crude product, which was then chromatographed to obtain 13,14-dihydro-15-keto-20-ethyl-PGE$_2$ isopropyl ester. Yield: 0.063 g (97%)

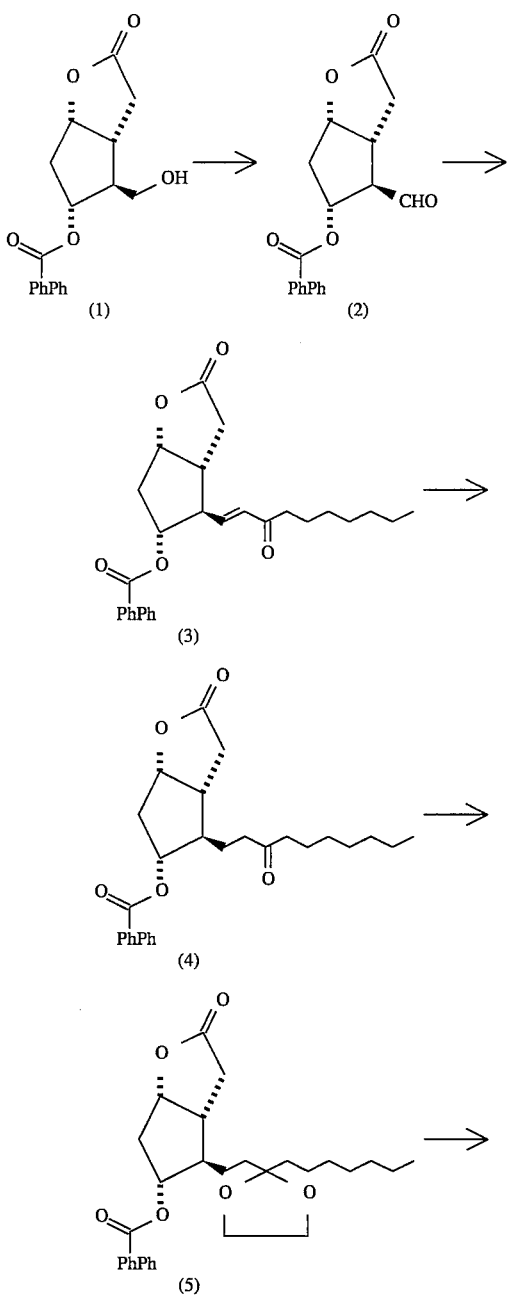

Synthesis chart I

-continued
Synthesis chart I

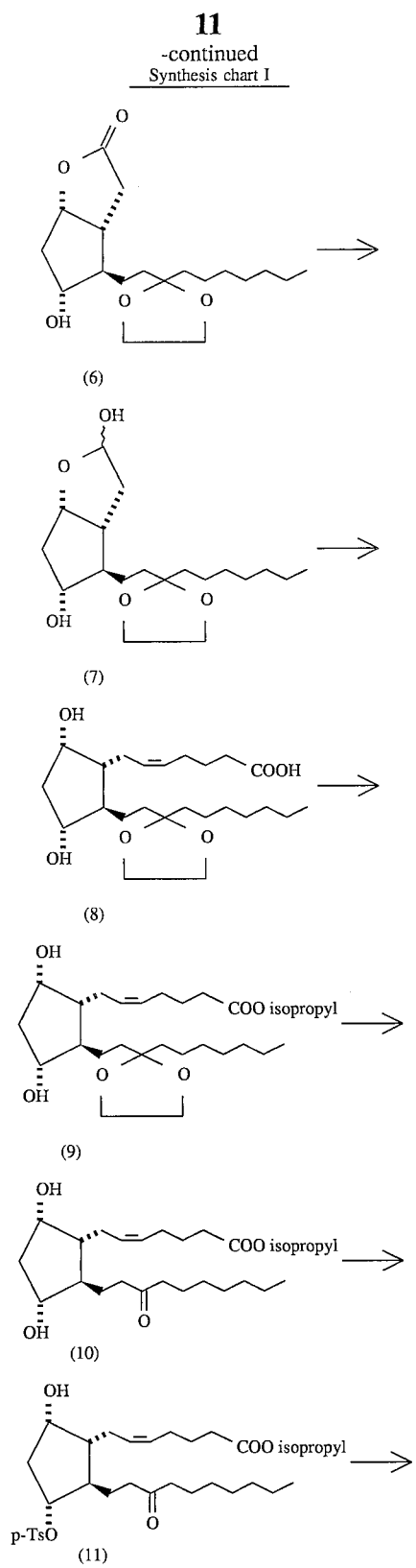

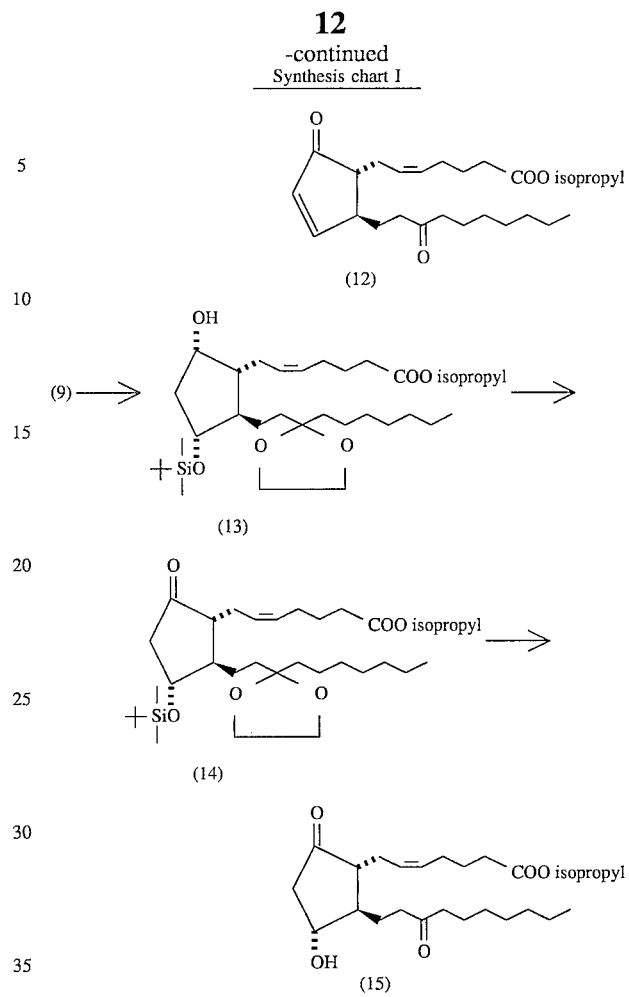

Experiment 1

13,14-dihydro-15-keto-20-ethyl-PGF$_2\alpha$ isopropyl ester having the moisture content of 0.11% by weight (hereinafter referred to as dry compound 1) was admixed with water in a predetermined amount (3.8%), and the mixture was shaken at room temperature for 2 hours to obtain 13,14-dihydro-15-keto-20-ethyl-PGF$_2\alpha$ isopropyl ester having the moisture content of 3.72% by weight (hereinafter referred to as hydrous compound 1).

Dry compound 1 and hydrous compound 1 were stored independently at 20° C. for 6 months (sealed and in dark), and then the content (% by weight) of 13,14-dihydro-15-keto-20-ethyl-PGF$_2\alpha$ isopropyl ester (hereinafter referred to as compound 1).

TABLE 1

|  | moisture content (% by weight) | Content of compound 1 (% by weight) | |
|---|---|---|---|
|  |  | Initial | End |
| Dry compound 1 | 0.11 | 99.4 | 92.2 |
| Hydrous compound 1 | 3.72 | 100.2 | 98.7 |

Based on the results obtained above, 13,14-dihydro-15-keto-20-ethyl-PGF$_2$α isopropyl ester, when stored in a hydrous condition (moisture content: 3.72%), exhibited almost no change in quality.

Experiment 2

Four groups of 13,14-dihydro-15-keto-20-ethyl-PGF$_2$α isopropyl ester having the moisture content of 0.00% by weight (hereinafter referred as dry compound 2) were stored in four desiccators at various degrees of relative humidity for 7 days respectively. After that, 13,14-dihydro- 15-keto-20-ethyl-PGF$_2$α isopropyl ester samples having moisture content corresponding to the relative humidities in the respective desiccators (hereinafter referred to as hydrous compounds 2, 3 or 4) were obtained. Dry compound 2 and hydrous compounds 2 to 4 were stored independently at 40° C. for 1 month (sealed and in dark), and then the content (% by weight) of 13,14-dihydro-15-keto-20-ethyl-PGF$_2$ isopropyl ester (hereinafter referred as compound 2) was determined. The results are shown in Table 2.

TABLE 2

| | moisture content (% by weight) | Content of compound 2 (% by weight) | |
|---|---|---|---|
| | | Initial | End |
| Dry compound 2 | 0.00 | 101.0 | 73.2 |
| Hydrous compound 2 | 2.39 (0.58)* | 100.0 | 93.7 |
| Hydrous compound 3 | 2.86 (0.69)* | 100.4 | 96.5 |
| Hydrous compound 4 | 4.14 (1.02)* | 100.7 | 97.8 |

*Values in bracket represent molar ratios (water/compound 2).

The molar ratios were obtained as follows.

Molar weight (water/compound 2)=[α/m]/[(100-α)/M]

wherein α is moisture content (%) of a compound, m is molecular weight of water and M is molecular weight of the compound. From the above results it is apparent that the stability of 13,14-dihydro-15-keto-20-ethyl-PGF$_2$α isopropyl ester is improved as moisture content increases.

Experiment 3

13,14-dihydro-15-keto-20-ethyl-PGF$_2$α isopropyl ester having the moisture content of 0.00% by weight (hereinafter referred to as dry compound 2) and emulsion of compound 2 in water (1.2 mg/ml) (hereinafter referred to as emulsion 1) were stored independently at 40° C. for 1 month (sealed and in dark), and then the content (% by weight) of 13,14-dihydro-15-keto-20-ethyl-PGF$_2$α isopropyl ester (hereinafter referred to as compound 2) was determined. The results are shown in Table 3.

TABLE 3

| | Content of compound 1 (% by weight) | |
|---|---|---|
| | Initial | End |
| Dry compound 2 | 101.0 | 73.2 |
| Emulsion 1 | 98.8 | 99.2 |

* Molar ratio of water:compound 2 in emulsion 1 is 19635:1.

From the above results, it is apparent that 13,14-dihydro-15-keto-20-ethyl-PGF$_2$α isopropyl ester, even when stored in the presence of excess amount of water, exhibited almost no change in quality.

Although the upper limit of moisture content in prostanoic acids according to the present invention is not critical, moisture content is generally 100,000 mole or less, preferably 50,000 mole or less, and more preferably, 20,000 mole or less.

What is claimed is:

1. A method of storing a prostanoic acid compound which comprises keeping a prostanoic acid compound represented by the following formula (I):

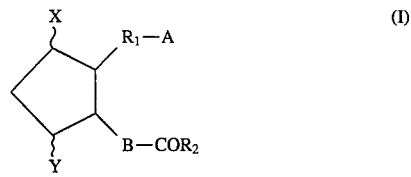

wherein
X and Y are hydrogen, hydroxy, halogen, lower alkyl, hydroxy(lower)alkyl or oxo (provided that at least one of X and Y is other than hydrogen, and the 5-membered ring may have at least one double bond);

A is COOH or a salt or ester thereof;

B is —CH$_2$—CH$_2$—, —CH=CH—, —C≡C—, —CH$_2$—CH$_2$—CH$_2$—, —CH$_2$—CH=CH—, —CH$_2$—C≡C—, —CH=CH—CH$_2$ or -C≡C—CH$_2$—;

R$_1$ is a divalent saturated or unsaturated lower or medium aliphatic hydrocarbon residue which is unsubstituted or substituted with a halo, oxo or aryl group;

R$_2$ is a saturated or unsaturated, lower or medium aliphatic hydrocarbon residue which is unsubstituted or substituted with halo, hydroxy, oxo, lower alkoxy, lower alkanoyloxy, cyclo (lower)alkyl, aryl or aryloxy group in the presence of sufficient water having open surface so that said compound has a moisture content of 1% or greater with the proviso that the molar ratio of water to the compound is 100,000:1 or less.

2. The method of claim 1, in which the prostanoic acid compound is a 13,14-dihydro-15-keto-prostaglandin.

* * * * *